United States Patent [19]

Castro et al.

[11] Patent Number: 5,089,474
[45] Date of Patent: Feb. 18, 1992

[54] NOVEL MICROPROTEINS

[75] Inventors: Bertrand Castro, St Aures; Dung Lenguyen, Montpellier; Anne Favel, Marseilles; Maria A. Previero, Montpellier, all of France

[73] Assignee: Roussel Uclaf, Paris, France

[21] Appl. No.: 528,834

[22] Filed: May 24, 1990

[30] Foreign Application Priority Data

May 31, 1989 [FR] France .................. 89 07155

[51] Int. Cl.$^5$ .................. A61K 37/02; A61K 37/64; C07K 1/04; C07K 7/10
[52] U.S. Cl. .................. 514/12; 530/324
[58] Field of Search .................. 530/324; 514/12

[56] References Cited

U.S. PATENT DOCUMENTS 4,485,100 11/1984 Hochstrasier et al. .............. 424/177
4,829,052 5/1989 Glover et al. .................. 514/12

FOREIGN PATENT DOCUMENTS 8603497 6/1986 PCT Int'l Appl.

*Primary Examiner*—Jeffrey E. Russel
*Assistant Examiner*—Stephen Walsh
*Attorney, Agent, or Firm*—Bierman and Muserlian

[57] ABSTRACT

A microprotein containing 28 amino acids of the formula

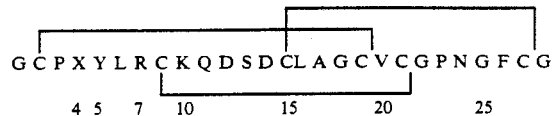

wherein the X in position 4 is a residue of a member of the group consisting of valine, leucine, isoleucine, norleucine, alanine, cyclohexylalanine, o-methylthreonine, phenylglycine or α-amino butyric acid, Arginine, Y in position 5 is a residue of isoleucine or serine, Z in position 7 is a residue of methionine or norleucine, with the proviso that Z is a norleucine residue when X is an Arginine residue, having anti-elastase activity.

20 Claims, No Drawings

NOVEL MICROPROTEINS

STATE OF THE ART

Related prior art includes Medline Abstracts No. 89-274,165 (Heitz) No. 89-233,599 (Favel) and No. 89-350,964 (Le-Nguyen) and Biological Abstract No. 37096274 (Le-Nguyen).

It is known that Ecballium elaterium seeds, more commonly known as "jumping gherkin", are a very important source of proteins which inhibit proteinases. Thus, one microprotein has in particular been isolated from these seeds known as EETI II (Ecballium elaterium Trypsin Inhibitor II) of the following structure:

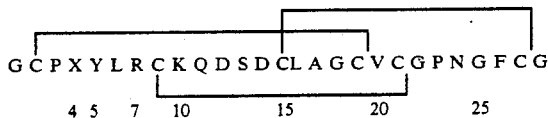

(Protease inhibitors from Ecballium elaterium seeds. A. Favel, H. Mattras, M.A. Coletti-Previero, R. Zwilling, E.A. Robinson & Castro. International Journal of Peptide & Protein Research. 1H 2D NMR and Distance Geometry of the folding of Ecballium elaterium, a member of the squash inhibitor family. A. Heitz, L. Chiche, D. Le-Nguyen & B. Castro, Biochemistry, (1989) 28, p. 2392, 2398).

The nomenclature used is that of the IUPAC-IUB commission (1984) European J. Biochem. 183, 9 to 37. This microprotein which contains 28 amino-acid residues, 3 disulfide bridges and 5 glycine residues particularly shows the property of inhibiting trypsin.

OBJECTS OF THE INVENTION

It is an object of the invention to provide the novel microproteins of formula I and a process for their preparation.

It is another object of the invention to provide anti-elastase compositions and a novel method of inducing anti-elastase activity in warm-blooded animals.

These and other objects and advantages of the invention will become obvious from the following detailed description.

THE INVENTION

The novel microproteins of the invention contain 28 amino acids of the formula

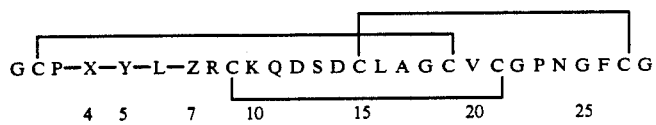

wherein the X in position 4 is a residue of a member of the group consisting of valine, leucine, isoleucine, norleucine, alanine, cyclohexylalanine, o-methyltheomine, phenylglycine or α-amino butyric acid, Arginine, Y in position 5 is a residue of isoleucine or serine, Z in position 7 is a residue of methionine or norleucine with the proviso that Z is a norleucine residue when X is an Arginine residue.

The present invention has replaced certain amino acid residues of EETI II to obtain novel microproteins in which the anti-trypsin activity of EETI II has disappeared to the benefit of an anti elastase activity both against bovine pancreatic elastase and against human leucocyte elastase. The novel products present also the advantage of being able to be prepared by total synthesis in large quantities.

Among the preferred microproteins of the invention are those wherein Y in position 5 is an isoleucine residue, those wherein Z in position 7 is a norleucine residue, and those wherein X in position 4 is a residue of valine, alanine or norleucine.

Among the more preferred microproteins of the invention those wherein X in position 4 is a valine residue, Y in position 5 is an isoleucine residue and Z in position 7 is a norleucine residue, those wherein X in position 4 is an alanine residue, Y in position 5 is an isoleucine residue and Z in position 7 is a methionine residue and those wherein X in position 4 is a norleucine residue, Y in position 5 is a serine residue and Z in position 7 is a methionine residue.

The novel process of the invention for the preparation of microproteins of formula I comprises sequentially introducing in a solid phase synthesis protected amino acids on a cross-linked oxymethyl polystyrene resin with a coupling agent, releasing the peptide chain formed from the resin, deprotecting the amino acids and cyclizing the 3 disulfide bridges to obtain the microprotein of formula I.

In a preferred method of the process, the cross-linked oxymethyl polystyrene resin is a "Boc-gly-CM" type resin wherein Boc is a tert-butoxy carbonyl, gly is glycine and CM is the crosslinked oxymethyl polystyrene resin, the coupling agent is BOP or (benzotriazol-1-yloxy) tris-(dimethylamino) phosphonium hexafluorophosphate and the release of the peptide chain from the resin as well as the deprotection of the amino-acids is carried out with hydrofluoric acid operating at low temperature.

The novel anti-elastase compositions of the invention are comprised of an anti-elastase effective amount of at least one microprotein of formula I and an inert pharmaceutical carrier or excipient. The compositions may be in the form of tablets, dragees, gelules, capsules, granulas, suppositories, ointments, injectable solution or suspensions and aerosols.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have a remarkable anti-elastase activity, both against bovine pancreatic elastase and against human leucocyte elastase and the anti-trypsin activity disappeared. They are useful in pneumology, for the treatment of emphysema, pneumonia, bronchitis, pulmonary disorders caused by nicotine poisoning or atmospheric pollution, in cardiology for the treatment of atherosclerosis, in rhumatology for the treatment of arthritis, as well as for example in dermatology for the treatment of psoriasis, burns, bullosis, and for ageing of the skin, in gastroenterology for the treatment of acute pancreatitis and generally for the treatment of all afflictions which involve the malfunotioning of elastase.

The novel method of the invention for inducing anti-elastase activity in warm-blooded animals, including humans, comprises administering to warm-blooded animals an anti-elastase effective amount of at least one microprotein of formula I. The microproteins may be administered orally, rectally, parenterally or topically. The usual daily dose is 0.013 to 4 mg/kg depending on the specific microprotein, the condition treated and the method of administration.

In the following examples there are described several preferred embodiments to illustrate the invention. However, it is to be understood that the invention is not intended to be limited to the specific embodiments.

EXAMPLE 1

Val-4, Nle-7 derivative

STEP A: Assembly of the peptide chain

A solid phase synthesis method was used with "Boc-Gly-CM" resin type which is a cross-linked oxymethyl polystyrene resin in which Boc is a tert-butoxy carbonyl, Gly is glycine and CM-resin is a cross-linked oxymethyl polystyrene resin. The resin containing 0.4 mmol of Gly/g was prepared by the cesium salt method with the technique of GISIN, BF (1973) Helv. Chim. Acta, Vol. 56, 1476 to 1482.

The protector groups of the amino acids were the following: p-methoxy benzyl for cysteine, cyclohexyl ester for aspartic acid, xanthyl for asparagine and glycine, tosyl for arginine, benzyl for serine, o-chlorobenzyloxycarbonyl for lysine and methionine was not protected.

The coupling reaction was carried out using BOP (benzotriazol1-yloxy tris (dimethylamino) phosphonium hexafluorophosphate and the coupling cycle can be summarized as follows:

Deprotection:
1—Washing with 30% trifluoroacetic acid in dichloromethane, one minute.
2—Deprotection with 30% trifluoroacetic acid in dichloromethane, 30 minutes.
3—Washing with 3% of ethanedithiol in isopropanol once.
4—Washing twice with dichloromethane.

Coupling:
1—Addition of Boc—amino acid and BOP complex,
2—Addition of diisopropylethylamine (4 equi . . . . ) then of solvent (dichloromethane or dimethylformamide) with stirring,
3—After negative reaction to ninhydrin, washing twice with dichloromethane.

For acetylation, the resin was treated with acetic anhydride/ dichloromethane (50/50 V/V) mixture for 15 minutes.

As the methionine was not protected, the last Boc-group was eliminated by trifluoroacetic acid before the treatment with hydrofluoric acid to avoid a tert-butylation. Thus, from 3 g of "BOC-Gly-CM-resin", there was obtained operating manually 9.5 g of protected peptide chain complex, which resin was used directly in the following step.

STEP B: Release of the protected peptide chain - resin complex 3 g of the protected peptide chain - resin complex of Step B were reacted for 60 minutes with 30 ml of hydrofluoric acid at 0° C. in the presence of(3 ml) of anisole and (1 ml) of dimethylsulfide. The resin was washed with ether and the crude peptide was extracted by a 20% aqueous solution of acetic acid. After lyophilization, 1.1 g of crude non-cyclized product were obtained, which was used directly in the following step.

STEP C: Cyclization and purification 400 mg of the crude peptide of Step B were dissolved in 350 ml of water and vigorously stirred. Diisopropyl ethylamine was added until a pH of 8 was obtained (one drop of mixture was recovered every hour and added to one drop of a solution containing dithiobis (2-nitrobenzoic) acid in a molar buffer of $K_2HPO_4$ (pH 8) to follow the oxidation reaction). During the whole reaction, the pH was maintained at 8 by addition of diisopropylethylamine. After 50 hours, the absence of yellow coloration was observed in the test with dithiobis (2-nitrobenzoic) acid. The product obtained was purified by high performance liquid chromatography (HPLC on a Whatman M20 ODS OP column and was eluted with a $CH_3CN/H_2O$ solution containing 0.1% trifluoroacetic acid. The fraction obtained was lyophilized to obtain 40 mg of the expected product. The composition in amino acids appears in Table 1 hereafter:

EXAMPLES 2 to 9

Using the procedure of Example 1, but with other amino acids, 8 other derivatives were prepared which appear in Table 1 hereafter. The composition in amino acids are also indicated in Table 1.

TABLE 1

| | PRODUCTS OF EXAMPLES | | | | | | | | |
|---|---|---|---|---|---|---|---|---|---|
| | 1 [Val4, Nle7] | 2 [Nle7] | 3 [Ala4, Nle7] | 4 [Ala4, | 5 [Phe4, Nle7] | 6 [Nle4, Nle7] | 7 [Nle4, Ser5, Nle7] | 8 Ser5 | 9 Ile5 |
| Asp | 2.9 | 3 | 3.1 | 3.3 | 2.4 | 2.8 | 3 | 2.8 | 2.9 |
| Glu | 1 | 1 | 1 | 1 | 1 | 1 | 1 | 1.1 | 1.1 |
| Ser | 1 | 0.9 | 1 | 0.9 | 1.1 | 1 | 1.8 | 1.9 | 0.9 |
| Gly | 5.4(6) | 5.7(6) | 6.4(6) | 6.6 | 5.2(6) | 4.7 | 4.25 | 5.9 | 6.1 |
| Arg | 1.1 | 2.1 | 1.2 | 1.2 | 1 | 1.3 | 1.17 | 1.1 | 1.1 |
| Ala | 1 | 1 | 2 | 2 | 1 | 1 | 1 | 1 | 1.1 |
| Pro | 2.25 | 2.1 | 2.75 | 2.6 | 2.1 | 2.2 | 2.1 | 2.1 | 2.2 |
| Val | 1.7 | 1.4 | 1.46 | 1.6 | 1.3 | 1.1 | 1 | 2.2 | 1.2 |
| Met | 0 | 0 | 0 | 0.8 | 0 | 0 | 0 | 0 | 0 |
| Ile | 1.63 | 1.2 | 1.3 | 1 | 2 | 2 | 2.1 | 1.1 | 1.9 |
| Leu | 2 | 2 | 2 | 2.1 | 2 | 2 | 2.1 | 2.1 | 2.1 |
| Phe | 1 | 1.3 | 1.3 | 1.6 | 2.3 | 1.5 | 1.6 | 1.1 | 1 |

TABLE 1-continued

| | PRODUCTS OF EXAMPLES | | | | | | | |
|---|---|---|---|---|---|---|---|---|
| | 1 [Val4, Nle7] | 2 [Nle7] | 3 [Ala4, Nle7] | 4 [Ala4] | 5 [Phe4, Nle7] | 6 [Nle4, Nle7] | 7 [Nle4, Ser5, Nle7] | 8 Ser5 | 9 Ile5 |
| Lys | 1 | 1 | 1 | 1 | 1.1 | 0.94 | 1 | 1 | 1.1 |

EXAMPLE 10

An injectable solute was prepared containing 1 mg of the product of Example 1 and 2 ml of sterile aqueous excipient.

EXAMPLE 11

Tablets were prepared containing 2 mg of the product of Example 1 and sufficient excipient of lactose, starch talc and magnesium stearate for a tablet weighing 150 mg.

EXAMPLE 12

An ointment was prepared containing 10 mg of the product of Example 1 and sufficient excipient for 100 mg.

STUDY OF ANTI-ELASTASE ACTIVITY

The anti-elastase activity was determined by spectrophotometric dosage vis-a-vis bovine elastase and vis-a-vis human leucocyte elastase by a technique similar to that described by Delmar Biochem., Vol. 19, p. 468, 1980. The results are in the following Table.

TABLE 2

| Dissociation constants of EETI analogs toward 2 serine proteases. | | |
|---|---|---|
| Products of Examples | Elastase | Human leucocyte elastase |
| 1 | $5 \times 10^{-6}$ M | $2 \times 10^{-9}$ M |
| 3 | $6 \times 10^{-7}$ M | $9 \times 10^{-8}$ M |
| 4 | $2.5 \times 10^{-8}$ M | $6 \times 10^{-8}$ M |
| 5 | | $2 \times 10^{-7}$ M |
| 6 | $3 \times 10^{-6}$ M | $2 \times 10^{-7}$ M |
| 7 | $8 \times 10^{-7}$ M | |
| 8 | | $2.5 \times 10^{-7}$ M |

Various modifications of the product and methods of the invention may be made without departing from the spirit or scope thereof and it is to be understood that the invention is intended to be limited only as defined in the appended claims.

What is claimed is:

1. A polypeptide containing 28 amino acids of the formula

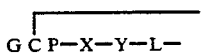

I wherein the X in position 4 is a residue of a member of the group consisting of valine, leucine, isoleucine, norleucine, alanine, cyclohexylalanine, o- methylthreonine, phenylglycine or α-amino butyric acid, Arginine, Y in position 5 is a residue of isoleucine or serine, Z in position 7 is a residue of methionine or norleucine with the proviso that Z is a norleucine residue when X is an Arginine residue.

2. A polypeptide of claim 1 wherein Y in position 5 is an isoleucine residue.

3. A polypeptide of claim 1 wherein X in position 4 is selected from a residue of the group consisting of valine, alanine and norleucine.

4. A polypeptide of claim 1 wherein Z in position 7 is a norleucine residue.

5. A polypeptide of claim 1 wherein X in position 4 is a valine residue, Y in position 5 is an isoleucine residue and Z in position 7 is a norleucine residue.

6. A polypeptide of claim 1 wherein X in position 4 is an alanine residue, Y in position 5 is an isoleucine residue and Z in position 7 is a methionine residue.

7. A polypeptide of claim 1 wherein X in position 4 is a norleucine residue, Y in position 5 is a serine residue and Z in position 7 is a methionine residue.

8. A process for the preparation of a polypeptide of claim 1 comprising squentially introducing in a solid phase synthesis protected amine acids on a cross-linked oxymethyl polystyrene resin with a coupling agent, releasing the peptide chain formed from the resin, deprotecting the amino acids and cyclizing the 3 disulfide bridges to obtain the microprotein of claim 1.

9. The process of claim 8 wherein the cross-linked oxymethyl polystyrene resin is Boc-Gly-CM resin wherein Boc is a tert-butoxy carbonyl, Gly is glycine and CM is the cross-linked oxymethyl polystyrene resin.

10. The process of claim 8 wherein the coupling agent is BOP or (benzotriazol-1-yloxy) tris(dimethylamino) phosphonium hexafluorophosphate.

11. The process of claim 8 wherein the release from the resin and the deprotection of the amino acids are effected with hydrofluoric acid at about 0° C.

12. An anti-elastase composition comprising an anti-elastase effective amount of at least one polypeptide of claim 1.

13. A composition of claim 12 wherein Y in the 5 position is an isoleucine residue.

14. A method of inducing anti-elastase activity in warm-blooded animals comprising administering to warm-blooded animals an anti-elastase effective amount of at least one polypeptide of claim 1.

15. A method of claim 14 wherein Y in position 5 is an isoleucine residue.

16. A method of claim 14 wherein X in position 4 is selected from a residue of the group consisting of valine, alanine and norleucine.

17. A method of claim 14 wherein Z in position 7 is a norleucine residue.

18. A method of claim 14 wherein X in position 4 is a valine residue, Y in position 5 is an isoleucine residue and Z in position 7 is a norleucine residue.

19. A method of claim 14 wherein X in position 4 is an alanine, residue, Y in position 5 is an isoleucine residue and Z in position 7 is a methionine residue.

20. A method of claim 14 wherein X in position 4 is a norleucine residue, Y in position 5 is a serine residue and Z in position 7 is a methionine residue.

* * * * *